US010216903B2

(12) United States Patent
Thomas et al.

(10) Patent No.: US 10,216,903 B2
(45) Date of Patent: Feb. 26, 2019

(54) MEDICAL ADHERENCE TRACKING FRAMEWORK

(71) Applicant: ORACLE INTERNATIONAL CORPORATION, Redwood Shores, CA (US)

(72) Inventors: Jayant Thomas, San Ramon, CA (US); Victor Matskiv, Walnut Creek, CA (US); Zhaogang Qian, Acton, MA (US); Vallabha Jagdish, San Ramon, CA (US)

(73) Assignee: ORACLE INTERNATIONAL CORPORATION, Redwood Shores, CA (US)

( * ) Notice: Subject to any disclaimer, the term of this patent is extended or adjusted under 35 U.S.C. 154(b) by 231 days.

(21) Appl. No.: 14/085,987

(22) Filed: Nov. 21, 2013

(65) Prior Publication Data

US 2015/0142458 A1 May 21, 2015

(51) Int. Cl.
G16H 40/40 (2018.01)
G16H 40/60 (2018.01)
G06F 19/00 (2018.01)

(52) U.S. Cl.
CPC .......... *G06F 19/3418* (2013.01); *G06F 19/00* (2013.01); *G06F 19/3456* (2013.01)

(58) Field of Classification Search
CPC ............... G06F 19/321; G06F 19/3418; G06F 19/3456; G06Q 50/24
USPC ........................................................ 705/2
See application file for complete search history.

(56) References Cited

U.S. PATENT DOCUMENTS

| 8,412,512 | B1 | 4/2013 | Mok et al. |
| 8,419,636 | B2 | 4/2013 | Brown |
| 8,543,351 | B2* | 9/2013 | Yuen ................. A61B 5/0002 702/160 |
| 8,566,121 | B2 | 10/2013 | Ramasubramanian et al. |
| 2002/0099273 | A1* | 7/2002 | Bocionek ............... A61B 5/411 600/300 |
| 2003/0046434 | A1* | 3/2003 | Flanagin ........... G06F 17/30581 709/248 |
| 2006/0074736 | A1* | 4/2006 | Shukla ................ G06Q 10/06 717/100 |
| 2006/0089542 | A1* | 4/2006 | Sands ................. A61B 5/4833 600/300 |
| 2008/0294996 | A1 | 11/2008 | Hunt et al. |
| 2009/0132636 | A1* | 5/2009 | Natanzon .............. G06F 19/321 709/201 |
| 2011/0145693 | A1* | 6/2011 | Mutic ................... G06F 19/321 715/233 |
| 2012/0270661 | A1 | 10/2012 | Smith et al. |
| 2013/0079128 | A1 | 3/2013 | Thomas et al. |

(Continued)

*Primary Examiner* — Hiep V Nguyen
(74) *Attorney, Agent, or Firm* — Potomac Law Group PLLC

(57) ABSTRACT

A system that implements a medical adherence tracker framework receives a workflow definition, the workflow definition comprising one or more tasks. The system persists the workflow definition, and the persisting includes serializing the workflow definition. The system synchronizes the workflow definition to one or more user devices, including transmitting the serialized workflow definition to the user devices. The workflow definition includes nested objects, and the system serializes the workflow definition and nested objects separately and links the serialized objects using an object identifier.

14 Claims, 4 Drawing Sheets

(56) References Cited

U.S. PATENT DOCUMENTS

2013/0179208 A1\* 7/2013 Chung ................... G06Q 10/06
                                                   705/7.15
2013/0291065 A1   10/2013 Jakowski et al.
2014/0143299 A1\* 5/2014 Klotzer ................. G06F 19/321
                                                    709/203

\* cited by examiner

MEDICAL ADHERENCE TRACKING FRAMEWORK

FIELD

One embodiment is directed generally to a computer system, and in particular to a computer system that manages a medical adherence tracking framework.

BACKGROUND INFORMATION

In medicine, "adherence" (also compliance or capacitance) describes the degree to which a patient correctly follows medical advice. Most commonly, it refers to medication or drug compliance, but it can also apply to other situations such as medical device use, self care, self-directed exercises, or therapy sessions.

Worldwide, non-compliance is a major obstacle to the effective delivery of health care. Estimates from the World Health Organization ("WHO") in 2003 indicate that only about 50% of patients with chronic diseases living in developed countries follow treatment recommendations. The figures are even lower with respect to adherence rates for preventative therapies, and can be as low as 28% in developed countries. In particular, low rates of adherence to therapies for asthma, diabetes, and hypertension are thought to contribute substantially to the human and economic burden of those conditions. This may affect patient health, and affect the wider society when it causes complications from chronic diseases, formation of resistant infections, or untreated psychiatric illness.

Compliance rates may be overestimated in the medical literature, as compliance is often high in the setting of a formal clinical trial but drops off in a "real-world" setting. For example, one study reported a 97% compliance rate at the beginning of treatment with statins, but only about 50% of patients were still compliant after six months.

SUMMARY

One embodiment is a system that implements a medical adherence tracker framework. The system receives a workflow definition, the workflow definition including one or more tasks. The system persists the workflow definition, and the persisting includes serializing the workflow definition. The system synchronizes the workflow definition to one or more user devices, including transmitting the serialized workflow definition to the user devices. The workflow definition includes nested objects, and the system serializes the workflow definition and nested objects separately and links the serialized objects using an object identifier.

DETAILED DESCRIPTION

One embodiment is a system that manages the tracking of user adherence to predetermined or user-defined workflows by providing a medical adherence tracker framework that enables the synchronization across multiple devices, such as mobile devices, of a user's progress in completing a workflow. Workflows can include one or more tasks to be executed right away or scheduled for future execution. The medical adherence tracker framework allows users to update workflow progress from any of their devices. The framework automatically detects workflow updates on any of the devices and then automatically synchronizes workflow updates across all the devices.

In one embodiment, the system manages the tracking of user adherence to medical workflows such as taking one or more medications on a predetermined or user-defined schedule, getting a predetermined or user-defined amount of sleep each night, drinking a predetermined or user-defined amount of water each day, etc.

Figure 1:
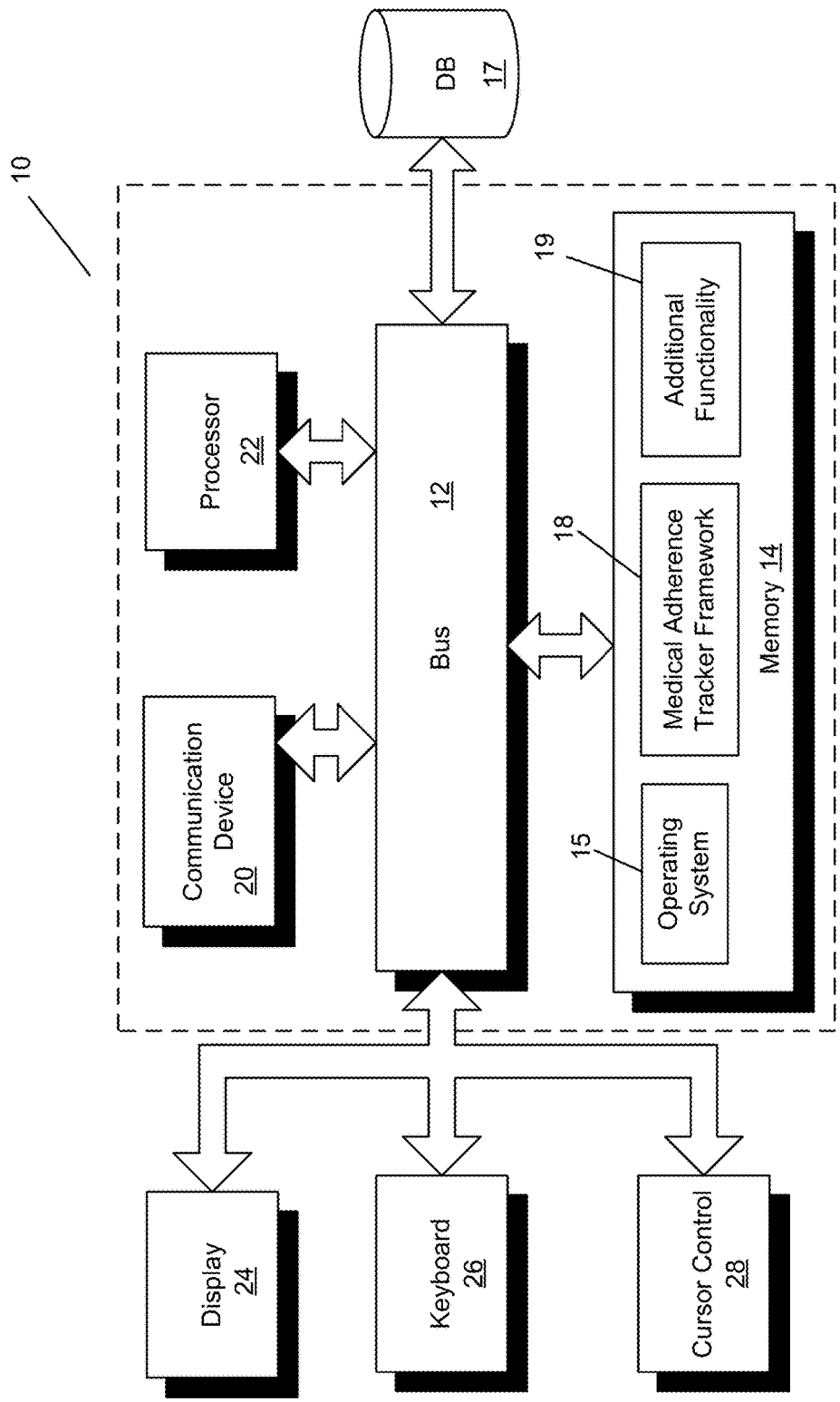
FIG. 1 is a block diagram of a computer system that can implement an embodiment of the present invention.

FIG. 1 is a block diagram of a computer system 10 that can implement an embodiment of the present invention. Although shown as a single system, the functionality of system 10 can be implemented as a distributed system. System 10 includes a bus 12 or other communication mechanism for communicating information, and a processor 22 coupled to bus 12 for processing information. Processor 22 may be any type of general or specific purpose processor. System 10 further includes a memory 14 for storing information and instructions to be executed by processor 22. Memory 14 can be comprised of any combination of random access memory ("RAM"), read only memory ("ROM"), static storage such as a magnetic or optical disk, or any other type of computer readable media. System 10 further includes a communication device 20, such as a network interface card, to provide access to a network. Therefore, a user may interface with system 10 directly, or remotely through a network or any other method.

Computer readable media may be any available media that can be accessed by processor 22 and includes both volatile and nonvolatile media, removable and non-removable media, and communication media. Communication media may include computer readable instructions, data structures, program modules or other data in a modulated data signal such as a carrier wave or other transport mechanism and includes any information delivery media.

Processor 22 is further coupled via bus 12 to a display 24, such as a Liquid Crystal Display ("LCD"), for displaying information to a user. A keyboard 26 and a cursor control device 28, such as a computer mouse, is further coupled to bus 12 to enable a user to interface with system 10.

In one embodiment, memory 14 stores software modules that provide functionality when executed by processor 22. The modules include an operating system 15 that provides operating system functionality for system 10. The modules further include a medical adherence tracker framework module 18 that provides medical adherence tracking capabilities, as disclosed in more detail below. System 10 can be part of a larger system, such as a database system or an enterprise resource planning ("ERP") system. Therefore, system 10 will typically include one or more additional functional modules 19 to include the additional functionality. A database 17 is coupled to bus 12 to provide centralized storage for modules 18, and 19 and store medical adherence tracking information, etc.

In one embodiment, system 10 is a mobile device configured to receive user input to create user workflows including one or more tasks, and track user adherence to the workflow tasks. In such embodiments, the user updates workflow progress through a user interface and the updated workflows are serialized and persisted on the mobile device and synchronized across the user's other devices. Reminders can be generated on the user's devices to encourage adherence to the workflows. Module 18 can be integrated with various third-party devices that can be used to track user adherence to workflows, such as the Flex, Zip, One, and Aria products by FitBit Inc., the Nike+ FuelBand product by Nike, Inc., blood pressure monitors, etc.

In some embodiments, system 10 is a server configured to receive user created workflows and synchronize the workflows across the user's mobile devices. In some such embodiments system 10 can provide an online web portal for users to view/update their workflows. In other such embodiments, system 10 can synchronize user workflows with another server to provide the online web portal for users to view/update their workflows.

Figure 2:
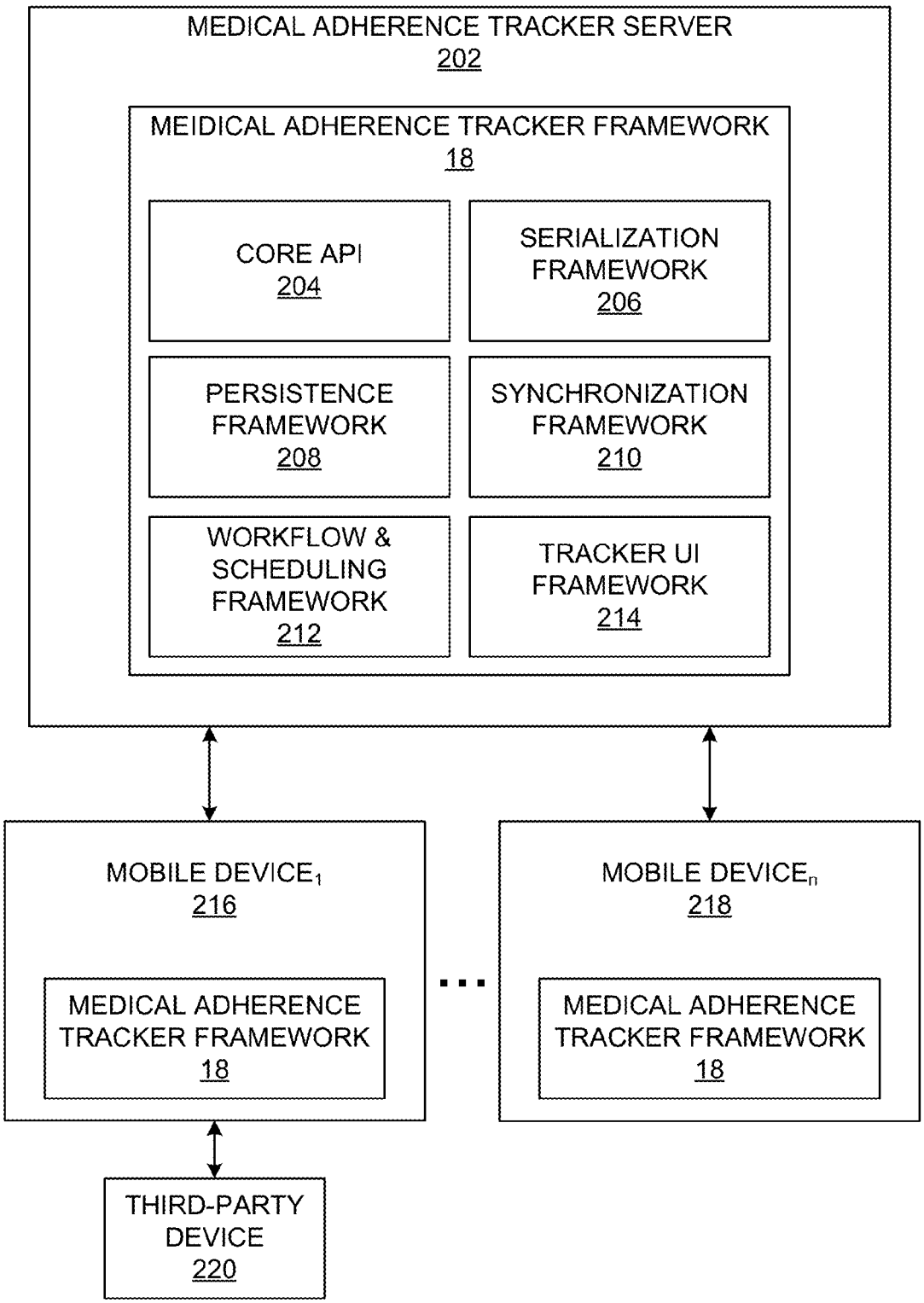
FIG. 2 is a block diagram illustrating the medical adherence tracker framework of FIG. 1 in accordance with one embodiment.

FIG. 2 is a block diagram illustrating a medical adherence tracker system in accordance with one embodiment. In such an embodiment, medical adherence tracker system 200 comprises medical adherence tracker server 202, mobile devices 216 and 218, and a third-party device 220. Medical adherence tracker server 202 provides medical adherence tracking of a user operating any of the mobile devices 216-218 and comprises a core API 204, a serialization framework 206, a persistence framework 208, a synchronization framework 210, a workflow and scheduling framework 212, and a tracker user interface ("UI") framework 214. Server 202 and/or devices 216, 218 can be implemented by system 10 of FIG. 1.

In some embodiments, each mobile device 216-218 can be configured to receive user input to create user workflows including one or more tasks and track user adherence to the workflow tasks. In such embodiments, if the user updates workflow progress through a user interface (tracker UI framework 214) on mobile device 216, the workflow updates are serialized (serialization framework 206) and persisted (persistence framework 208) on mobile device 216 and synchronized (synchronization framework 210) across the user's other mobile devices, such as mobile device 218, by medical adherence tracker server 202. Mobile devices 216 and 218 can generate and display reminders (workflow and scheduling framework 212) to encourage user adherence to the workflows. Mobile device 216 can be integrated with third party device 220 to track user adherence to workflows. Examples of third party device 220 include Flex, Zip, One, and Aria by FitBit Inc., Nike+ FuelBand by Nike, Inc., and blood pressure monitors.

Mobile device 216 can include integration interfaces that can be directly or indirectly integrated with one or more third party device 220. For example, in some embodiments, third party device 220 is a FitBit product that does not provide a direct interface to mobile devices, and instead data from the FitBit product is synchronized to a FitBit server first via proprietary FitBit interfaces and then a FitBit integration interface included in mobile device 216 can access the data on the FitBit server via a public FitBit API. In some embodiments, medical adherence tracker server 202 can include one or more integration interface modules, such as the FitBit integration interface described above, to access data generated by third party device 220 on the server side of the tracker framework. The modules can be configured to directly or indirectly receive a data feed from third party device 220 (e.g., an indirect data feed can be achieved via an integration interface module such as that described above for FitBit products). The data is then stored in the tracker framework object graph on the server side (e.g., medical adherence tracker server 202) and subsequently synchronized to mobile device 216. In some embodiments, mobile device 216 can be directly integrated with third party device 220 and directly receive data generated by third party device 220 which can then be stored on mobile device 216 and subsequently synchronized to medical adherence tracker server 202.

In some embodiments, medical adherence tracker server 202 can be configured to receive user created workflows and synchronize (synchronization framework 210) the workflows across the user's mobile devices. Although not shown, in some embodiments, medical adherence tracker server 202 can provide a web portal for users to view/update their workflows. In some embodiments, medical adherence tracker server 202 can synchronize user workflows with another server (not shown) that provides the web portal for users to view/update their workflows.

Referring to the components of medical adherence tracker framework 18, in embodiments, core API 204 comprises common protocols and interfaces that are used by frameworks 206-214, such as an object protocol and interface, QDLObject, a reference interface, QDLReference, and a collection protocol, QDLCollection.

In such embodiments, QDLObject is a fundamental protocol and conforming interface that describes a basic framework object that allows for the setting of arbitrary properties (not known at compile time) and exposes properties such as:
    objectId (unique object identifier ("GUID"));
    parentId (optional parent object identifier); and
    delegates (a collection of delegates interested in this object's behaviors).

In such embodiments, QDLReference describes serializable object references and QDLCollection describes a basic framework collection of QDLObject objects.

In embodiments, serialization framework 206 provides for first class native language objects (e.g., instances of Objective-C classes, such as instances of QDLObject) to be serialized into a format that can be stored, such as the JavaScript Object Notation ("JSON") format, and vice versa on a server or a mobile device, such as mobile device 202. Unlike standard iOS Objective-C serialization APIs that permit serialization of only a limited set of classes (such as NSDictionary, NSArray, etc.), serialization framework 206 provides for serializing instances of custom Objective-C classes, such as instances of QDLObject. In some embodiments, serialization framework 206 includes the JSON specification and serialization APIs that follow the JSON specification.

In one embodiment, medication adherence can be tracked using a Medication Adherence Tracker object. For example, below is a sample representation of a Medication Adherence Tracker object in JSON format:

```
{
    "type" : "Tracker",
    "subject" : "Medication",
    "trackables" : {
        "refId" : "8A633298-7E30-4554-AD92-D030FF5662E9",
        "type" : "QDLReference"
    },
    "missedEventThreshold" : 3600,
    "name" : "MedicationAdherenceTracker",
    "reminder" : {
        "type" : "Reminder",
        "persistent" : 0
    },
    "metadata" : {
        "refId" : " MedicationAdherenceTracker ",
        "type" : "QDLReference"
    },
```

-continued

```
    "events" : {
        "refId" : "AB845125-FFE9-4122-A354-D28E2D235E88",
        "type" : "QDLReference"
    },
    "objectId" : "D0F420FD-0569-46EB-81C7-8A13D23D3071",
    "timelineDuration" : 86400,
    "schedule" : {
        "type" : "QDLSchedule",
        "recurrenceRule" : "FREQ=DAILY;BYHOUR=0",
        "startDate" : "2013-08-14T00:00:00GMT-07:00",
        "nextScheduledDate" : "2013-08-15T00:00:00GMT-07:00"
    }
}
```

In embodiments, persistence framework 208 provides for storing arbitrary objects in persistent storage on a server or a mobile device, such as mobile device 216. Unlike the standard iOS Core Data framework, persistence framework 208 does not require object storage structure to be pre-defined for any new type of object (i.e., the typical step of defining entities, tables etc. is not required).

Persistence framework 208 persists any object as long as it can be serialized using serialization framework 206. The internal data storage format is generic and does not change from one object type to another. In some embodiments, persistence framework 208 stores data in SQLite database tables. Upon creation, each object is assigned a globally unique identifier ("GUID"), and the identifier never changes. It is a responsibility of the entire ecosystem using the framework to assure global uniqueness of the identifier across all interested parties (i.e., across all mobile devices, web clients, servers capable of creating GUIDs). For each persistent object, a separate database record is created, and the database record includes, for example, object GUID (stored in a text column), an object in a serialized format that can be encrypted using, for example, the Advanced Encryption Standard ("AES") algorithm and a 256-bit key ("AES-256"), several timestamps, an object synchronization state ("OSS") and an object update identifier ("OUI"). Object update identifier can be used for object synchronization purposes with external systems.

In some embodiments, persistence framework 208 provides for object update/change auto-detection and auto-save. Unlike iOS Core Data, persistence framework 208 is capable of detecting updates/changes in the object content regardless of the object internal structure. Upon detecting the change, persistence framework 208 persists the changes automatically (i.e., without requiring an explicit "save" operation to be invoked after a change). In such embodiments, persistence framework 208 can be used to persist objects transparently without requiring programs to explicitly persist objects in their code. For example, when writing programs that use persistence framework 208, programmers can write code that deals with persistent objects the same way as with any other Objective-C language object, and no special treatment, such as the above mentioned explicit "save," is required when using persistence framework 208.

Persistence framework 208 provides for objects to be referenced from within other objects such that the objects can be persisted in a distributed fashion (i.e., instead of storing an object in a single BLOB with a complex hierarchy, such hierarchy can be split into separate sub-hierarchies, and each sub-hierarchy can be stored individually). For example, the following serialized Medication Tracker object:

```
{
    "type" : "Tracker",
    "objectId" : "D0F420FD-0569-46EB-81C7-8A13D23D3071",
    "subject" : "Medication",
    ...
    "events" : {
        "refId" : "AB845125-FFE9-4122-A354-D28E2D235E88",
        "type" : "QDLReference"
    },
}
``` references the following serialized Medication Tracker Events collection object:

```
{
    "type" : "QDLTransientCollection",
    "policy" : {
        "type" : "QDLTransientCollectionPolicy"
    },
    "parentId" : "D0F420FD-0569-46EB-81C7-8A13D23D3071",
    "description" : "Medication Tracker Events",
    "objectId" : "AB845125-FFE9-4122-A354-D28E2D235E88"
}
``` and each object can be serialized and stored (persisted) separately by persistence framework 208. In this example, the Medication Tracker Events object is a nested or child object of the Medication Tracker (parent) object, and "objectId" and "refId" of the serialized Medication Tracker object are linked, respectively, to "parentId" and "objectId" of the serialized Medication Tracker Events collection object. Persistent object referencing in this manner provides the capability of converting a single object having nested objects into an object graph. Such a graph can be distributed across systems and can also provide for flexible "delta"-based synchronization.

In some embodiments, when synchronizing object changes between systems, only modified portions ("delta") need to be synced This can be important for mobile systems, where bandwidth or network connection speed may be low or reduced and where network connections are inherently unreliable, because it reduces the amount of data to be transmitted to/from a mobile device, reduces the amount of time spent transmitting updates since less data is transmitted, and/or reduces the possibility of failure during transmission by reducing the amount of data transmitted.

In some embodiments, an object graph is configured such that the most frequently changed parts are represented by separate object(s) (object graph nodes), which can be configured to further reduce the amount of data (delta portions) that need to be synced when a change occurs.

Persistence framework 208 also provides features to query the objects in the persistent store based on criteria that can be defined using standard criteria predicates (e.g., using an iOS predicate framework, such as the NSPredicate Foundation class).

In embodiments, synchronization framework 210 provides for the synchronization of an object graph between one or more user devices and one or more servers. In some embodiments, data synchronized between user device and server is serialized using serialization framework 206 into a JSON format using the same format that is used for object persistent storage by persistent framework 208. For example, in some embodiments, when persistent framework 208 auto-detects a change in an object and persists that object (and the change), synchronization framework 210 can then be called to synchronize the change across other user devices and/or servers.

In some embodiments, synchronization framework 210 can rely on the Object Update Identifier ("OUI") stored in the persistent storage described above. OUI is a globally unique 64-bit numeric identifier assigned on the server when an object is synchronized from a mobile device (sent) to the server for the very first time. Afterwards, OUI is incremented every time the object is updated on the server. Since OUI is globally unique across the entire population of synchronizable objects, the size of the increment is arbitrary.

In some embodiments, synchronization framework 210 can rely on the Object Synchronization State ("OSS") indicator stored in the persistent storage described above. OSS is a numeric flag that allows synchronization framework 210 to determine if an object is synchronized (OSS=0) or still needs to be synchronized (OSS>0).

In some embodiments, synchronization framework 210 allocates a dedicated background thread to perform synchronization activities on a mobile device without affecting (or blocking) the main user interface thread. In such embodiments, by confining all synchronization activities to a single thread, synchronization framework 210 ensures such activities are to be processed serially in the order they were originally scheduled.

In some embodiments, synchronization framework 210 can perform the following synchronization operations:
  Fetch object graph updates from the server (this activity is performed on a regular basis, e.g., every minute while the mobile application/device is active);
  Send individual modified objects to the server (this activity is performed upon object change, i.e., as a result of object change auto detection); and
  Send unsynchronized objects to the server (this activity is performed on a regular basis, e.g., every minute while the mobile app is active. However under normal scenarios, unsynchronized objects are sent to the server by the individual sync operation above, so this operation is mainly for housekeeping/error recovery purposes).

In some embodiments, synchronization framework 210 can perform various optimizations of the synchronization operations. For example, when the same object is modified multiple times, synchronization framework 210 is capable of coalescing multiple update operations of the object into one, thus reducing synchronization network overhead. This becomes possible because of the delayed execution nature of the sync operations: instead of performing sync upon object change immediately, synchronization framework 210 can aggregate the change and perform a sync when certain conditions are met (e.g., when aggregation timeout expires or number of pending changes reaches certain threshold, whichever comes first).

In embodiments, workflow and scheduling framework 212 provides facilities to describe and execute various tasks on a user device, such as mobile device 216. Tasks can be organized into workflows, executed right away or scheduled for future execution.

In some embodiments, tasks, workflows, execution and scheduling aspects are described in a declarative fashion using a JSON-based programming metalanguage. An advantage of this approach is that the workflows can be defined on the server and then uploaded to a user device, such as mobile device 216, for execution, all without any modification of the user/mobile application code. This aspect can be useful when implementing application gamification concepts, because it provides flexibility for the application designer to describe gamification strategies (such as user "quests" or "missions") in a form of an uploadable workflow. The declarative nature of workflows makes it easier for the designer to introduce new features; it minimizes engineering involvement and thus reduces time to market of the features by essentially decoupling feature development lifecycle from the user/mobile application development lifecycle.

In embodiments, tracker UI framework 214 provides visual UI components that measure various aspects of human daily life (i.e., amount of sleep, physical activities, user medication, logging unplanned events, etc.). Tracker UI framework 214 provides a hosting structure as well as basic building blocks to create trackers.

In some embodiments, the tracker UI used on a mobile device, such as mobile device 216, can be log based or dial based. Dial based trackers are optimized for touch input and smaller screen sizes. Tracker UI framework 214 provides facilities to support and resolve potentially conflicting user touch gestures, for example swiping trackers horizontally and drag-and-drop of tracking elements.

In some embodiments, tracker UI framework 214 can be used standalone. In other embodiments, tracker UI framework 214 can be integrated with frameworks 204-211, as described in FIG. 3 below.

Figure 3:
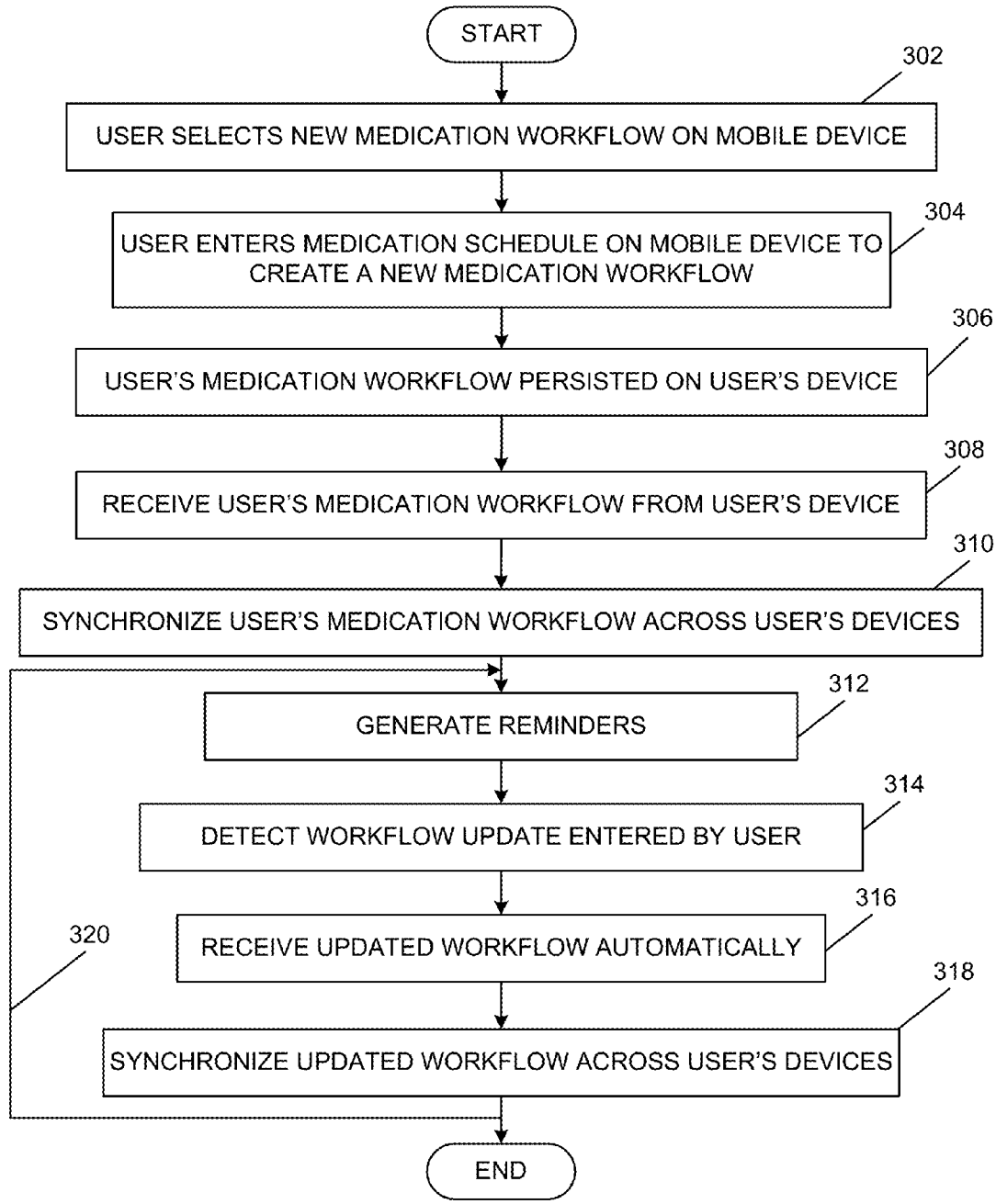
FIG. 3 is a flow diagram showing the functionality of the medical adherence tracker framework of FIG. 1 in accordance with one embodiment.

FIG. 3 is a flow diagram showing the functionality of medical adherence tracker framework module 18 of FIG. 1 in accordance with one embodiment. In one embodiment, the functionality of the flow diagram of FIG. 3 is implemented by software stored in memory or other computer readable or tangible medium, and executed by a processor. In other embodiments, the functionality may be performed by hardware (e.g., through the use of an application specific integrated circuit ("ASIC"), a programmable gate array ("PGA"), a field programmable gate array ("FPGA"), etc.), or any combination of hardware and software.

At 302, a user selects, on a mobile device, to create a new medication workflow. In some embodiments, tracker UI framework 214 can provide the user interface for creating the new medication workflow. Additional types of workflows can be supported, such as those shown in FIG. 4 below.

At 304, the user enters their medication schedule on the mobile device to create a new medication workflow.

At 306, module 18 persists the new medication workflow on the mobile device using persistence framework 208.

At 308, module 18 receives, at a server, the new medication workflow created on the user's mobile device. In some embodiments, the new medication workflow can be transmitted from the mobile device to the server using synchronization framework 210.

At 310, module 18 synchronizes the new medication workflow across the user's mobile devices using synchronization framework 210. In some embodiments, events, such as when to take a medication, are generated by scheduling framework 212, persisted by persistence framework 208, and synchronized across devices and server(s) by synchronization framework 210. In such embodiments, synchronizing the events allows the user to view and/or track his/her information/progress on other mobile device(s). In some embodiments, a medication tracker dial can be provided by tracker UI framework 214 that displays to a user their scheduled medications for a time period, such as a day.

At 312, module 18 generates reminders using scheduling framework 212 and the reminders are displayed to the user on one or more of the user's mobile devices. In some embodiments, reminders are generated using scheduling framework 212 on each of user's mobile devices.

At 314, module 18 automatically detects a change made to the new medication workflow on a user's mobile device. For example, the user can indicate on the mobile device that a pill has been taken, causing the medication workflow to be updated to reflect this new condition. After being updated, persistence framework 208 automatically detects the update and synchronization framework 210 transmits the update to the server.

At 316, module 18 receives the updated medication workflow from the mobile device.

At 318, module 18 synchronizes the updated medication workflow across the user's mobile devices using synchronization framework 210.

It will be appreciated that operations 302-318 may be repeated in whole or in part (an example of which is indicated by line 320) to create new workflows, synchronize the new workflows and/or updates to existing workflows, and/or generate reminders.

Figure 4:
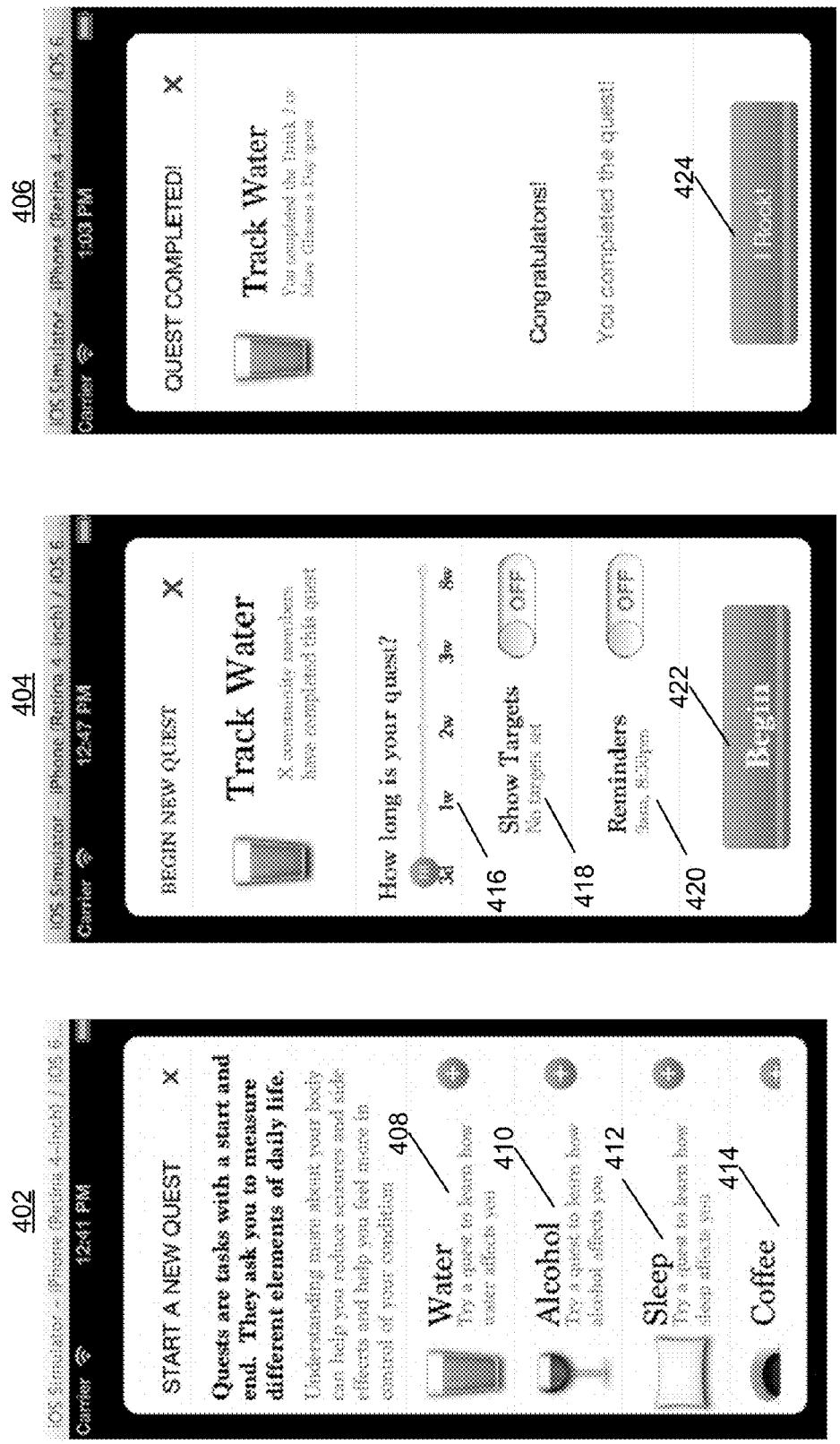
FIG. 4 illustrates an example mobile application implementing the medical adherence tracking framework of FIGS. 1 and 2 in accordance with one embodiment.

FIG. 4 illustrates an example mobile application implementing medical adherence tracking framework 18 of FIGS. 1 and 2 in accordance with one embodiment. The mobile application can include a start quest (or "workflow") screen 402, a begin quest screen 404, and a complete quest screen 406.

Start quest screen 402 can include a list of available quests (or workflows) such as a water quest 408, an alcohol quest 410, a sleep quest 412, and/or a coffee quest 414.

If a user selects to begin a water quest, begin quest screen 404 can be displayed and the user can select one or more desired water quest parameters to be applied, such as length of quest 416, show targets 418, and enable reminders 420. The user can begin the water quest using the desired parameters by selecting begin 422. For example, water quest 408 can be a workflow in medical adherence tracker framework 18 with tasks to drink a user-selectable target amount water each day (targets 418) for a user-selectable number of days (length of quest 416).

In some embodiments, when the user creates/begins/updates a water quest, the workflow for the water quest can be persisted and synchronized across the user's devices according to the processes described above in FIGS. 1-3.

Complete quest screen 406 can be shown when the user completes a water quest. In some embodiments, the user can earn rewards for completing quests and the user can view any rewards earned for completing the water quest by selecting button 424.

In some embodiments, applications implementing medical adherence tracking framework 18 of FIGS. 1 and 2 can utilize a user interface such as those disclosed in U.S. patent application Ser. No. 13/955,331, filed on Jul. 31, 2013, entitled "User Interface for Tracking Health Behaviors," the contents of which is hereby incorporated by reference in its entirety.

Referring again to FIG. 2, particular embodiments of components 204-214 of medical adherence tracker framework 18 will be described in detail, with example definitions written in the Objective-C programming language.

As discussed above, in some embodiments, core API 204 includes an object protocol and interface, "QDLObject", a reference interface, "QDLReference", and a collection protocol, "QDLCollection".

An example definition of QDLObject is provided below:

```
@protocol QDLObject <NSobject, QDLSerializable>
@optional
@property (nonatomic, retain) NSMutableArray *delegates;
@property (nonatomic, copy) NSString *objectId;
@property (nonatomic, copy) NSString *parentId;
-
(id<QDLTaskContext>)contextWithParent:(id<QDLTaskContext>)parent;
- (id)valueForKey:(NSString*)key;
- (void)setValue:(id)value forKey:(NSString*)key;
```

-continued
```
- (BOOL)assignValue:(id)value forKeyPath:(NSString*)keyPath;
- (NSMethodSignature *)methodSignatureForSelector:(SEL)aSelector;
+ (NSSet*)transientProperties;
+ (NSDictionary*)unwrappableKeyPaths;
@end
@interface QDLObject : NSObject<QDLObject /*, QDLTaskDelegate*/>
@property (nonatomic, retain) id<QDLTask> initTask;
@property (nonatomic, retain) NSMutableArray *delegates;
- (void)prepareInContext:(id<QDLTaskContext>)context;
+ (NSSet*)propertiesNotAffectingDirtyState;
@end
```

An example definition of QDLReference is provided below:

```
@interface QDLReference : NSProxy<QDLSerializable,
QDLObjectDelegate>
@property (nonatomic, copy) NSString *refId;
+ (id)asReference:(id<QDLObject>)object;
- (id)init;
- (id)initWithRefId:(NSString*)refId;
- (id)serialize;
- (id)deserializeInContext:(QDLSerializationContext*)context;
- (id)serializeInContext:(QDLSerializationContext*)context;
- (void)addObserver(NSObject *)anObserverforKeyPath:(NSString
*)keyPath
    options:(NSKeyValueObservingOptions)options context:(void
    *)context;
@end
```

An example definition of QDLCollection is provided below:

```
@protocol QDLCollection <QDLObject>
- (void)addObject:(id<QDLObject>)object;
- (void)removeObject:(id<QDLObject>)object;
- (id)objectWithId:(NSString*)objectId;
- (NSArray*)objects;
@optional
- (NSInteger)count;
- (id)objectAtIndex:(NSInteger)index;
- (NSUInteger)countByEnumeratingWithState:(NSFastEnumerationState
*)state
    objects:(id *)stackbuf count:(NSUInteger)len;
@end
```

In some embodiments, serialization framework 206 includes a protocol that enables serialization support for objects, "QDLSerializable", an interface that can define runtime context for performing serialization, "QDLSerializationContext", an interface that can provide high level typing abstraction over standard objective C class types, "QDLType", and an interface that is a singleton type resolution facility, "QDLTypeRegistry" (e.g., given the type name (specified in the JSON object representation with "type" attribute), it provides corresponding QDLType instance).

An example definition of QDLSerializable is provided below:

```
@class QDLSerializationContext;
@protocol QDLSerializable <NSObject>
@optional
- (id)serializeInContext:(QDLSerializationContext*)context;
- (id)deserializeInContext:(QDLSerializationContext*)context;
- (BOOL)shouldSerializeProperty:(NSString*)propertyName
inContext:(QDLSerializationContext*)context;
@end
```

An example definition of QDLSerializationContext is provided below:

```
typedef id (^NewInstance) (NSString*);
typedef id (^NewDictionaryInstance) (void);
typedef id (^NewArrayInstance) (void);
@interface QDLSerializationContext : NSObject
@property (nonatomic, retain) id typeKey;
@property (nonatomic, retain) NSString *dateFormat;
@property (nonatomic, copy) NewInstance newInstance;
@property (nonatomic, copy) NewDictionaryInstance
newDictionaryInstance;
@property (nonatomic, copy) NewArrayInstance newArrayInstance;
@property (nonatomic, retain) id currentObject;
@property (nonatomic, readonly) NSSet *delayedInitializers;
- (void)addDelayedInitializerForTarget:(id)target
        keyPath:(NSString*)keyPath
    variableName:(NSString*)variableName;
- (QDLSerializationContext*)push; //:(QDLSerializationContext*)parent;
- (void)pop;
- (void)setValue:(id)value forVariable:(NSString*)variableName;
- (id)valueForVariable:(NSString*)variableName;
@end
```

An example definition of QDLType is provided below:

```
@interface QDLType : NSObject
- (id)initWithClassName:(NSString*)className;
- (id)newInstance;
- (Class)typeClass;
@end
```

An example definition of QDLTypeRegistry is provided below:

```
@interface QDLTypeRegistry : NSObject
+ (QDLType*)typeFromName:(NSString*)typeName;
@end
```

In some embodiments, persistence framework 208 includes a persistent object protocol, "QDLPersistentObject", and a persistent object proxy interface, "QDLPersistentObjectProxy".

In embodiments, objects should support QDLPersistentObject to support persistence, but objects are not required to support this protocol directly because persistence framework 206 can create a proxy for each persistent object it manages (using, e.g., QDLPersistentObjectProxy). The proxy interface, QDLPersistentObjectProxy, adopts the QDLPersistentObject protocol. In such embodiments, the persistence framework 208 does not allow programmers using the framework to deal with "raw" persistence objects directly, instead "wrapping" them using QDLPersistentObjectProxy. QDLPersistentObjectProxy can be responsible for handling persistence object lifecycle, such as reacting to internal and external object changes.

An example definition of QDLPersistentObject is provided below:

```
typedef enum {
    QDLPersistentObjectStateSynchronized,
    QDLPersistentObjectStateModified,
    QDLPersistentObjectStateNew,
    QDLPersistentObjectStateUnknown,
} QDLPersistentObjectState;
#define QDLObjectChangedNotification
    @"QDLObjectChangedNotification"
#define QDLObjectAddedNotification @"QDLObjectAddedNotification"
#define QDLObjectRemovedNotification
    @"QDLObjectRemovedNotification"
#define QDLObjectStateChangedNotification
    @"QDLObjectStateChangedNotification"
@protocol QDLPersistentObject <QDLObject>
@property (nonatomic, assign) QDLPersistentObjectState state;
@property (nonatomic, assign) BOOL isDeleted;
@property (nonatomic, retain) NSDate *timestamp;
@property (nonatomic, retain) NSDate *createdTimestamp;
@property (nonatomic, assign) long long int updateId;
@property (nonatomic, retain) NSString *userId;
@optional
- (id)unwrap:(Class)targetClass;
@end
```

An example definition of QDLPersistentObjectProxy is provided below:

```
@interface QDLPersistentObjectProxy : NSProxy<QDLPersistentObject,
QDLObjectDelegate> {
    id<QDLObject> _object;
}
- (id)initWithObject:(id<QDLObject>)object;
- (id)initWithObject:(id<QDLObject>)object
state:(QDLPersistentObjectState)state;
@end
```

In some embodiments, persistence framework 208 includes an interface, "QDLPersistentStore", for interfacing with SQLite database(s) and isolating ("black-boxes") the low-level SQLite database operations from a user by providing a higher level abstraction API QDLPersistentStore interface. QDLPersistentStore can provide the following features: transaction management; retrieving object by objectId (e.g., the GUID described above); searching objects by their parentId; storing objects; updating objects; and querying objects that satisfy given criteria.

In some embodiments, instances of QDLPersistentStore can be bound (confined) to a thread that created them and should be used normally only from within that thread. The currentStore class method can be used to retrieve persistent store associated with the current thread. If there is no persistent store associated with the current thread, the currentStore method can create it and bind to the thread.

An example definition of QDLPersistentStore is provided below:

```
@interface QDLPersistentStore : NSObject
@property (atomic, assign) BOOL isValid;
+ (void)closeAll;
- (void)open;
- (void)close;
- (void)beginTransaction;
- (void)commit;
- (void)rollback;
- (id/*<QDLPersistentObject>*/)objectWithId:(NSString*)objectId;
- (NSArray*)objectsWithParentId:(NSString*)parentId limit:(NSInteger)limit;
```

-continued

```
- (void)addObjectsWithParentId:(NSString*)parentId
                  to:(id)collection
             orderBy:(NSString*)orderBy
               limit:(NSInteger)limit;
- (NSDictionary*)dictionaryForRecordWithId:(NSString*)objectId;
- (long long int)maxUpdateId;
- (long long int)maxUpdateId:(NSString*)userId;
- (id/*<QDLPersistentObject>*/)addObject:(id)object;
-
(id/*<QDLPersistentObject>*/)createPersistentObjectFromTemplate:(NSString*)t
emplateId;
/**
* This method should be used to retrieve all unsynchronized objects either
* in "new" or "modified" state and perform a custom operation on each object,
* for example send it to the server.
*/
- (void)enumerateUnsynchronizedObjectsUsingBlock:(void
(^)(id<QDLPersistentObject> object, NSUInteger idx, BOOL *stop))block;
- (void)enumerateObjectsWithPredicate:(NSPredicate*)predicate
                 usingBlock:(void (^)(id<QDLObject> object, NSUInteger idx,
                 BOOL *stop))block;
- (void)enumerateObjectsWithType:(NSString*)objectType
             predicate:(NSPredicate*)predicate
             usingBlock:(void (^)(id<QDLObject> object, NSUInteger idx,
             BOOL *stop))block;
- (void)enumerateObjectsOnMainThreadUsingPredicate:(NSPredicate*)predicate
                          withBlock:(void (^)(id<QDLObject> object,
                          NSUInteger idx, BOOL *stop))block
                          completion:(void (^)(BOOL completed))completion;
/**
* This method is for local updates only.
* It updates the following
* - parent_id (e.g. when object is inserted into a transient collection
* - object_sync_state
* - value (blob)
*
* Conflict resolution
*
* If object update id does not match stored one?
* It happens when
* 1) object update_id null, the stored update_id is not null.
*    Object is created on the device and then sent to the server, where it
     assigned
*    an external_object_id and update_id, then it synced back to the device
* 2) Same as #1 above, plus the object has been updated from another device
     after objectId assignement
*    Behavior: this method will override parent_id, sync state and value blob,
     without changing
*    external_object_id, update_id
* 3) object update_id != stored update_id, update_id != null, stored update_id !=
     null
*    object has been updated from another device.
*    Behavior: this method will override parent_id, sync state and value blob,
     without changing
*    external_object_id, update_id
*/
- (void)updateObject:(id/*<QDLPersistentObject>*/)object;
/**
* Updates object's externalObjectId, parentId, updateId, isDeleted, value.
* This method should be used for external sync (server->device).
*
* Notes to caller:
*
* The caller should perform intelligent delta analysis
* prior to calling this method in order to send proper notification, e.g. do
*    select * from all_objects where object_id = {objectId}
* first.
* If object is found, then perform an action per changed fields according
* to the following table:
*
*    Changed fields                    Action
* externalObjectId, updateId           Notification is not required
* parentId, isDeleted                  Collection notification is required
* value                                Object notification is required
*
* If object is not found, invoke another method, say addObject,
* and send collection notification
*
*/
```

-continued

```
- (void)updateObjectWithId:(NSString*)objectId
        parentId:(NSString*)parentId
        updateId:(int64_t)updateId
        isDeleted:(BOOL)isDeleted
            value:(id)value;
- (void)mergeObjectWithId:(NSString*)objectId
        parentId:(NSString*)parentId
        updateId:(int64_t)updateId
        userId:(NSString*)userId
     createdDate:(NSDate*)createdDate
       isDeleted:(BOOL)isDeleted
            value:(id)value;
- (void)updateObject:(NSString*)objectId
     state:(QDLPersistentObjectState)state
   ifNotChangedAfter:(NSDate*)timestamp;
/**
* Changes object_sync_state flag to QDLPersistentObjectStateSynchronized.
* This method should be used after synchronizing an object to the server.
*/
- (void)markObjectSynchronized:(id<QDLPersistentObject>)object;
+ (QDLPersistentStore*)currentStore;
+ (NSString*)createObjectId;
+ (NSString*)orderByClauseForSortDescriptors:(NSArray*)sortDescriptors
            withUnwrappableKeyPaths:(NSDictionary*)keyPaths;
@end
```

In some embodiments, persistence framework 208 includes an interface, "QDLQuery", to support predicate-based queries on objects stored by framework 206, and a protocol, "QDLQueryBuilder", to create and configure QDLQuery instances using an object oriented builder pattern.

An example definition of QDLQueryBuilder is provided below:

```
@protocol QDLQueryBuilder <NSObject>
- (id<QDLQueryBuilder>)withObjectType:(NSString*)objectType;
- (id<QDLQueryBuilder>)withPredicate:(NSPredicate*)predicate;
- (id<QDLQueryBuilder>)withGroupByBlock:(id
( )(id object))groupByBlock;
- (id)createQuery;
@end
@interface QDLQuery : NSObject
+ (id<QDLQueryBuilder>)queryBuilder;
- (id)execute;
@end
```

In some embodiments, persistence framework 208 includes an interface, "QDLMetadataRegistry", that represents a global metadata registry. Metadata can represent an object prototype ("sample") that is used to create actual object instances. Metadata itself can be persisted in the persistent store. For example, creating objects from metadata is one of the available options for object creation.

An example definition of QDLMetadataRegistry is provided below:

```
@interface QDLMetadataRegistry : NSObject<QDLCollectionDelegate>
+ (void)reset;
+ (QDLMetadataRegistry*)registry;
+ (void)initialize2;
- (NSArray*)metadataWithCategory:(NSString*)categoryName;
- (id)metadataWithId:(NSString*)metadataId;
@end
```

In some embodiments, persistence framework 208 includes an interface, "QDLPersistentContext," that is a high level abstraction on top of the persistent store (QDLPersistentStore) interface described above. QDLPersistentContext can further isolate users from the SQLite database(s). QDLPersistentContext can also provide a mechanism to create objects through a convenience object factory protocol, "QDLPersistentObjectFactory".

In embodiments, the following options are available for object creation:
  Creating an object from metadata object (e.g., by using the "withMetadata" method below);
  Creating an object by specifying its metadata object name (e.g., by using the "withName" method below); and
  Creating an object by specifying its objective C class (e.g., by using the "withClass" method below).

It can be possible to set object extra object properties upon creating object with any of the 3 methods below.

An example definition of QDLPersistentObjectFactory is provided below:

```
@protocol QDLPersistentObjectFactory <NSObject>
- (id<QDLPersistentObjectFactory>)withMetadata:(QDLMetadata*)metadata;
- (id<QDLPersistentObjectFactory>)withName:(NSString*)name;
- (id<QDLPersistentObjectFactory>)withClass:(Class)class;
- (id<QDLPersistentObjectFactory>)withParentId:(NSString*)parentId;
- (id<QDLPersistentObjectFactory>)withObjectId:(NSString*)objectId;
- (id<QDLPersistentObjectFactory>)withProperty:(NSString*)name
value:(id)value;
- (id<QDLPersistentObjectFactory>)withProperties:(NSDictionary*)properties;
- (id)createObject;
- (id)createCollection;
@end
@interface QDLPersistentContext : NSObject
```

```
+ (QDLPersistentContext*)context;
- (id<QDLPersistentObjectFactory>)objectFactory;
- (id)createObjectFromMetadata:(QDLMetadata*)metadata;
- (id)createObject:(NSString*)metadataId;
- (id/*<QDLPersistentObject>*/)registerObject:(id<QDLObject>)object;
- (id)objectWithid:(NSString*)objectId;
- (NSArray*)objectsWithParentId:(NSString*)parentId limit:(NSInteger)limit;
- (void)updateObject:(id<QDLPersistentObject>)object;
- (void)beginTransaction;
- (void)commit;
- (void)rollback;
@end
```

In some embodiments, persistence framework 208 includes an interface, "QDLTransientCollection", that represents persistent data collections. In such embodiments, the collection object itself is a persistent object and, as any persistent object, has a unique object id and the elements of the collection (nested or child objects) are stored independently from the parent collection and refer to the parent collection object id using a parentId property (one-directional relationship). In such embodiments, the collection does not explicitly reference its child (or nested) elements.

An example definition of QDLTransientCollection is provided below:

```
@interface QDLTransientCollection : QDLObject<QDLCollection,
NSFastEnumeration>
@end
```

In some embodiments, persistence framework 208 includes an interface, "QDLTransientPriorityCollection", which, similar to QDLTransientCollection, has a unique object id, does not reference its child elements explicitly, and its child elements refer this collection using their parentId property. However, unlike QDLTransientCollection, QDLTransientPriorityCollection represents a partial snapshot of its children elements. The child elements elected to be a part of this snapshot are based on their ordering priority (defined by orderBy property). The size of the snapshot can be limited to cacheSize. QDLTransientPriorityCollection can provide functionality that is conceptually similar to a priority cache.

An example definition of QDLTransientPriorityCollection is provided below:

```
@interface QDLTransientPriorityCollection :
QDLObject<QDLCollection>
@property (nonatomic, assign) NSInteger cacheSize;
@property (nonatomic, copy) NSString *orderBy;
@property (nonatomic, copy) NSString *primaryStorageType;
- (BOOL)hasMore;
- (void)update;
@end
```

In some embodiments, synchronization framework 210 includes an interface, "QDLBackgroundProcessor", that represents a thread that performs generic (not necessarily sync related) tasks in background, and a protocol, "QDLBackgroundProcessorDelegate", that represents a delegate. QDLBackgroundProcessor can be used as a dedicated thread that performs synchronization in a background (without blocking a user interface). If an instance of QDLBackgroundProcessorDelegate protocol is provided to QDLBackgroundProcessor (via delegate property), the delegate will be handled pending tasks for preparation and/or final processing.

An example definition of QDLBackgroundProcessorDelegate is provided below:

```
@protocol QDLBackgroundProcessorDelegate <NSObject>
@optional
- (void)prepareTasks:(NSMutableArray*)tasks;
- (void)processTasks:(NSMutableArray*)tasks;
@end
```

An example definition of QDLBackgroundProcessor is provided below:

```
@interface QDLBackgroundProcessor : NSThread
@property (nonatomic, assign) NSInteger maxBufferSize;
@property (nonatomic, assign) NSTimeInterval maxBufferingTimeout;
@property (nonatomic, retain) id<QDLBackgroundProcessorDelegate>
delegate;
- (void)addTask:(id<QDLTask>)task;
- (void)scheduleShutdown;
@end
```

In some embodiments, synchronization framework 210 can comprise a protocol, SyncTask, that synchronization tasks can adopt.

An example definition of SyncTask is provided below:

```
@protocol SyncTask <NSObject>
@property (nonatomic, copy) NSString *userId;
@property (nonatomic, readonly) id coalesceId;
- (BOOL)canBeSkippedInTasks:(NSArray*)tasks;
@end
```

In some embodiments, synchronization framework 210 can include an interface, "SyncManager", that coordinates the synchronization activities in the framework (e.g., fetching and updating objects, handling dedicated sync thread). In some embodiments, SyncManager should be explicitly started and stopped using start and stop method respectively.

An example definition of SyncManager is provided below:

```
@interface SyncManager :
NSObject<QDLBackgroundProcessorDelegate>
@property (nonatomic, copy) NSString *syncUrl;
@property (nonatomic, copy) NSString *userId;
- (void)start;
- (void)stop;
@end
```

In some embodiments, synchronization framework 210 can include an interface, "FetchAllObjectsSyncTask", that represents a task that synchronizes objects from a server to the mobile device. FetchAllObjectsSyncTask can request from the server objects with Object Update Id ("OUID") greater than maximum OUID stored on the device. In some embodiments, FetchAllObjectsSyncTask can be the only task that can bring data from the server, and each execution of this task can bring just the changes since the previous execution (e.g., a delta update), thereby minimizing the network overhead.

An example definition of FetchAllObjectsSyncTask is provided below:

```
@interface FetchAllObjectsSyncTask : NSObject<QDLTask, SyncTask>
@property (nonatomic, copy) NSString *url;
@property (nonatomic, assign) BOOL notificationsEnabled;
@property (nonatomic, retain) NSNumber *debugMaxUpdateId;
@end
```

In some embodiments, synchronization framework 210 can include an interface, "UpdateUnsyncedObjectsSyncTask", that represents a task that synchronizes objects in unsynchronized state (sync state>0) from the mobile device to the server. Objects can be synchronized to the server right upon change by another dedicated task (e.g., UpdateObjectSyncTask), so UpdateUnsyncedObjectsSyncTask can be used for housekeeping and error recovery purposes.

An example definition of UpdateUnsyncedObjectsSyncTask is provided below:

```
@interface UpdateUnsyncedObjectsSyncTask : NSObject<QDLTask, SyncTask>
@property (nonatomic, copy) NSString *url;
@end
```

In some embodiments, synchronization framework 210 can include an interface, "UpdateObjectSyncTask", that, when an object is updated on a device, can be scheduled to synchronize the update back to the server. In some embodiments, if multiple such tasks are scheduled for the same object, they are subject to coalescing.

An example definition of UpdateObjectSyncTask is provided below:

```
@interface UpdateObjectSyncTask : NSObject<QDLTask, SyncTask>
@property (nonatomic, copy) NSString *url;
- (id)initWithObjectId:(NSString*)objectId;
@end
```

In some embodiments, workflow and scheduling framework 212 can include a protocol and interface, "QDLSchedulable", that schedulable objects must adopt (or use the interface).

An example definition of QDLSchedulable protocol is provided below:

```
@protocol QDLSchedulable <NSObject>
- (NSDate*)nextScheduledDate;
- (id)run:(id)context;
@optional
- (NSArray*)schedulables;
@end
```

An example definition of QDLSchedulable interface is provided below:

```
@interface QDLSchedulable : QDLObject<QDLSchedulable>
- (id)runWithDate:(NSDate*)date
inContext:(id<QDLTaskContext>)context;
@property (nonatomic, retain) QDLSchedule *schedule;
@property (nonatomic, copy) NSString *scheduleCompletionCondition;
@end
```

In some embodiments, workflow and scheduling framework 212 can include an interface, "QDLScheduler", that represents a scheduler that works with objects adopting QDLSchedulable Protocol/Interface.

An example definition of QDLScheduler is provided below:

```
@interface QDLScheduler : NSObject
- (id)initInContext:(id<QDLTaskContext>)context;
- (void)addSchedulable:(id<QDLSchedulable>)schedulable;
- (void)removeSchedulable:(id<QDLSchedulable>)schedulable;
- (void)stop;
@end
```

In some embodiments, workflow and scheduling framework 212 can include an interface, "QDLSchedule", that represents a recurring schedule that can be defined, for example, in Request for Comments ("RFC") 2445 format (e.g., iCalendar). QDLSchedule can support both statefull or stateless scheduled event enumeration.

An example definition of QDLSchedule is provided below:

```
@interface QDLSchedule : QDLObject<NSCoding>
@property (nonatomic, retain) NSDate *nextScheduledDate;
@property (nonatomic, copy) NSString *recurrenceRule;
@property (nonatomic, retain) id startDate;
- (id)initWithRecurrenceRuleString:(NSString*)rule
startDate:(NSDate*)startDate;
- (void)enumerateEventsBefore:(NSDate*)date
withBlock:(void (^)(NSDate*,
BOOL*))block;
- (void)enumerateEventsUntil:(NSDate*)date
withBlock:(void (^)(NSDate*, BOOL*))block;
- (void)enumerateEventsFrom:(NSDate*)startDate before:(NSDate*)date
withBlock:(void (^)(NSDate*, BOOL*))block;
- (void)enumerateEventsFrom:(NSDate*)startDate until:(NSDate*)date
withBlock:(void (^)(NSDate*, BOOL*))block;
- (id<QDLDateIterator>)iteratorWithStartDate:(NSDate*)startDate;
- (void)resetToDate:(NSDate*)date;
@end
```

In some embodiments, workflow and scheduling framework 212 can include a protocol, "QDLTask", that can represent a framework task.

An example of QDLTask is provided below:

```
@protocol QDLTask;
@protocol QDLTaskDelegate <NSObject>
- (void)task:(id<QDLTask>)task
didRunInContext:(id<QDLTaskContext>)context
withResult:(QDLTaskResult*)result;
@end
```

Another example definition of QDLTask is provided below:

```
@protocol QDLTask </*QDLObject, */ NSObject>
- (QDLTaskResult*)run:(id<QDLTaskContext>)context;
@optional
```

-continued

```
@property (nonatomic, assign) NSMutableArray *delegates;
@end
```

In some embodiments, workflow and scheduling framework 212 can include a protocol and interface, "QDLTaskContext", that can describe a context in which workflow tasks are executed. For example, tasks can use context as a media to exchange information by setting and reading context values. Contexts can form a hierarchy and a context can be constructed by specifying its parent context.

An example definition of QDLTaskContext is provided below:

```
@protocol QDLTaskContext <NSObject>
@optional
- (id)valueForKey:(NSString *)key;
- (id)valueForKeyPath:(NSString *)keyPath;
- (void)setValue:(id)value forKeyPath:(NSString *)keyPath;
- (id)valueForUndefinedKey:(NSString *)key;
- (void)setValue:(id)value forUndefinedKey:(NSString *)key;
/**
* Note: This method does NOT behave the same way as
setValue:forKeyPath:
* Flow:
* 1) Check if the embedded object can be assigned the value
* 2) If not, invoke the same method recursively on the parentContext
*/
- (void)assignValue:(id)value forKeyPath:(NSString*)keyPath;
@end
@interface QDLTaskContext : NSObject<QDLTaskContext>
+ (QDLTaskContext*)contextWithObject:(id)object
   inParentContext:(id<QDLTaskContext>)parentContext;
@end
```

In some embodiments, workflow and scheduling framework 212 can include an interface, "QDLFlow", that can describe basic sequential execution of tasks and can be a task itself (e.g., can adopt QDLTask protocol described above).

An example definition of QDLFlow is provided below:

```
@interface QDLFlow : QDLObject<QDLTask, QDLTaskDelegate> {
   QDLFlowTask *_firstTask;
}
@property (nonatomic, assign) NSArray *tasks;
- (void)addTask:(id<QDLTask>)task;
@end
```

In some embodiments, workflow and scheduling framework 212 can include an interface, "QDLConditionalTask", that can represent a task that can be executed only if a provided condition is true.

An example of QDLConditionalTask is provided below:

```
@interface QDLConditionalTaskResult : QDLTaskResult
+ (QDLConditionalTaskResult*)resultWithBool:(BOOL)boolValue;
@property (nonatomic, readonly) BOOL taskDidRun;
@end
@interface QDLConditionalTask : QDLObject<QDLTask,
QDLTaskDelegate>
@property (nonatomic, retain) id<QDLTask> task;
@property (nonatomic, copy) NSString *condition;
/**
* Returns QDLConditionalTaskResult(YES) if the task was evaluated, i.e.
condition applied, otherwise NO
*/
- (id /*QDLConditionalTaskResult**/)run:(id<QDLTaskContext>)context;
@end
```

In some embodiments, workflow and scheduling framework 212 can include an interface, "QDLSwitchTask", that is conceptually analogous to a C-language switch. QDLSwitchTask can be derived from the QDLFlow, and when executing set of conditional tasks (e.g., QDLConditionTask above), it stops execution as soon as it executes a first task with condition evaluated to true.

```
@interface QDLSwitchTask : QDLFlow
@end
```

In some embodiments, workflow and scheduling framework 212 can include an interface, "QDLLoopTask", that is conceptually similar to C-language loop. The internal task is executed repeatedly as long as predicate-based condition evaluates to true.

An example of QDLLoopTask is provided below:

```
@interface QDLLoopTask : QDLObject<QDLTask>
@property (nonatomic, retain) id<QDLTask> task;
@property (nonatomic, copy) NSString *condition;
@end
```

In some embodiments, tracker UI framework 214 can include an interface, "TrackerControl", that represents basic abstract class for all trackers, and a delegate interface, "TrackerControlDelegate". TrackerControl can provide some basic functionality, such as supporting gesture recognition as well as drag and drop operations.

An example definition of TrackerControlDelegate is provided below:

```
@protocol TrackerControlDelegate <NSObject>
@optional
- (void)tracker:(TrackerControl*)tracker
didRecognizeTapOnObject:(id)object at:(CGPoint)location;
- (void)tracker:(TrackerControl*)tracker
didRecognizeLongPressOnObject:(id)object
withState:(UIGestureRecognizerState)state at:(CGPoint)location;
- (void)tracker:(TrackerControl*)tracker
didRecognizeDoubleTapOnObject:(id)object at:(CGPoint)location;
- (void)tracker:(TrackerControl*)tracker didZoom:(CGFloat)scale;
@end
```

An example definition of TrackerControl is provided below:

```
@interface TrackerControl : InteractionObject<Zoomable,
UIGestureRecognizerDelegate> {
   UIView *_view;
}
@property (nonatomic, readonly) UIView *view;
@property (nonatomic, retain) TrackerControlModel *model;
@property (nonatomic, assign) id/*<TrackerDelegate>*/ trackerDelegate;
@property (nonatomic, readonly) NSMutableArray *allObjects;
@property (nonatomic, readonly) DragDropManager *dragDropManager;
@property (nonatomic, readonly) UITapGestureRecognizer
*tapGestureRecognizer;
@property (nonatomic, readonly) UITapGestureRecognizer
*doubleTapGestureRecognizer;
@property (nonatomic, readonly) UILongPressGestureRecognizer
*longPressGestureRecognizer;
@property (nonatomic, readonly) UIView *placeholderView;
- (id)initWithPlaceholderView:(UIView*)placeholderView;
- (id)objectAtLocation:(CGPoint)location;
- (void)activateAfterDelay:(CGFloat)delay;
- (void)tap:(UITapGestureRecognizer*)recognizer;
- (void)doubleTap:(UITapGestureRecognizer*)recognizer;
```

-continued

```
- (void)longPress:(UILongPressGestureRecognizer*)recognizer;
@end
```

In some embodiments, tracker UI framework 214 can include a protocol and interface, "TrackerControlModel", that represents a basic object model behind the UI component.

An example definition of TrackerControlModel (protocol) is provided below:

```
@protocol TrackerControlModel;
@protocol TrackingModelDelegate <NSObject>
@optional
- (void)model:(id<TrackerControlModel>)model
didAddElement:(id)element;
- (void)model:(id<TrackerControlModel>)model
didRemoveElement:(id)element;
- (void)modelDidChange:(id<TrackerControlModel>)model;
@end
```

An example definition of TrackerControlModel (interface) is provided below:

```
@protocol TrackerControlModel <NSObject, Insightful>
- (NSArray*)elements;
- (void)addElement:(id<TrackingModelElement>)element;
- (void)removeElement:(id<TrackingModelElement>)element;
- (void)removeAllElements;
@optional
- (id)unwrap:(Class)targetClass;
@end
```

Another example definition of TrackerControlModel (interface) is provided below:

```
@interface TrackerControlModel : NSObject<TrackerControlModel,
TrackingModelElementDelegate> {
    NSMutableArray *_elements;
}
@property (nonatomic, readonly) NSMutableArray *delegates;
@property (nonatomic, retain) NSString *name;
@property (nonatomic, retain) NSString *title;
@property (nonatomic, assign) BOOL trackerPlus;
- (id)initWithElements:(NSArray*)elements;
+ (TrackerControlModel*)plusModel;
@end
```

In some embodiments, tracker UI framework 214 can include an interface, "TrackerControlFactory", that represents a factory to create tracker control objects.

An example definition of TrackerControlFactory is provided below:

```
@interface TrackerControl Factory : NSObject
+ (UIView*)createPlaceholderCircleView;
- (id)initWithUserProfile:(UserProfile*)userProfile;
-
(TrackerControl*)createTrackerForModel:(TrackerControlModel*)model;
@end
```

In some embodiments, tracker UI framework 214 can include an interface, "TimelineTrackerControl", that represents a timeline tracker control.

An example definition of TimelineTrackerControl is provided below:

```
typedef TimelineEventObject* (^CreateTimelineObject)
(id<TimelineEvent>);
typedef void (^DropObjectAtTimeline) (TrackerControl*, id, NSInteger);
@interface TimelineTrackerControl : TrackerControl<Zoomable,
DraggableDelegate, TrackingModelDelegate>
@property (nonatomic, assign) TimelineStartPoint timelineStartPoint;
@property (nonatomic, retain) TrackingSubject *trackingSubject;
@property (nonatomic, assign) NSInteger totalUnits;
@property (nonatomic, assign) NSInteger intervalUnits;
@property (nonatomic, assign) NSInteger
acceptableDropRadiusDeviation;
@property (nonatomic, retain) TrackerControlModel *model;
@property (nonatomic, assign) CGPoint clockCenter;
@property (nonatomic, retain) UIView *timelineView;
@property (nonatomic, retain) UIView *dialView;
@property (nonatomic, readonly) UIView *placeholderView;
@property (nonatomic, assign) BOOL dropAtTimelineEnabled;
@property (nonatomic, assign) BOOL subjectTapEnabled;
@property (nonatomic, copy) CreateTimelineObject
timelineObjectForEvent;
@property (nonatomic, copy) DropObjectAtTimeline
dropObjectAtTimelineHandler;
- (id)initWithPlaceholderView:(UIView*)placeholderView;
@end
```

In some embodiments, tracker UI framework 214 can include an interface, "TrackingSubject", that represents a tracking subject, normally displayed in the middle of the tracker control dial. Tracker subjects can expose certain interaction behavior (e.g., can be dragged from the middle to the edge of the dial and beyond).

An example definition of TrackingSubject is provided below:

```
@interface TrackingSubject : InteractionObject<Draggable> {
    UIView *_view;
}
@property (nonatomic, assign) BOOL isPlusable;
@property (nonatomic, assign) BOOL draggingEnabled;
- (id)initWithParentObject:(id<InteractionObject>)parentObject
        image:(UIImage*)image;
-(BOOL)isPlusable;
@end
```

In some embodiments, tracker UI framework 214 can include an interface, "TimelineEventObject", that represents an interactive UI event (e.g., a "bubble" overlay) displayed on the edge of the tracker control dial.

An example definition of TimelineEventObject is provided below:

```
@interface TimelineEventObject : InteractionObject<Draggable, Rotatable,
TimelineEventDelegate>
@property (nonatomic, readonly) id<TimelineEvent> timelineEvent;
```

```
@property (nonatomic, readonly) UIView<Rotatable> *view;
- (id)initWithTimelineEvent:(id<TimelineEvent>)event
eventStateMetadataFactory:(TimelineEventStateMetadataFactory*)timelineEvent
StateMetadataFactory
        timelineTracker:(TimelineTrackerControl*)tracker
    distanceFromCenter:(DistanceFromCenter2)distanceFromCenter;
- (id)initWithTimelineEvent:(id<TimelineEvent>)event
            view:(UIView<Rotatable,TimelineEventView>*)view
    timelineTracker:(TimelineTrackerControl*)tracker
    distanceFromCenter:(DistanceFromCenter2)distanceFromCenter;
- (void)adjustLocationToIntervalForAngle:(CGFloat)angle;
@end
```

In some embodiments, tracker UI framework 214 can include an interface, "TimelineEvent", that represents a model for basic event object for "TimelineTrackerControl", and a protocol, "TimelineEventDelegate", that can be a delegate.

An example definition of TimelineEventDelegate is provided below:

```
@protocol TimelineEventDelegate <NSObject>
@optional
- (void)event:(id<TimelineEvent>)event stateChangedTo:(id)newState;
- (void)event:(id<TimelineEvent>)event
didAddLinkedEvent:(id<TimelineEvent>)linkedEvent;
- (void)event:(id<TimelineEvent>)event
didRemoveLinkedEvent:(id<TimelineEvent>)linkedEvent;
@end
```

An example definition of TimelineEvent is provided below:

```
@protocol TimelineEvent <TrackingModelElement>
@property (nonatomic, assign) NSInteger units;
@optional
@property (nonatomic, assign) NSInteger linkedEventCount;
@optional
@property (nonatomic, retain) TimelineEventState eventState;
@optional
- (NSInteger)removeLastLinkedTrackerEventAndReturnCountBeforeRemove;
@end
```

An example definition of TimelineEvent is provided below:

```
@interface TimelineEvent : TrackingModelElement<TimelineEvent>
@property (nonatomic, assign) NSInteger units;
@end
```

In some embodiments, tracker UI framework 214 can include a protocol, "Draggable", that describes draggable objects.

An example definition of Draggable is provided below:

```
@protocol Draggable;
@protocol DraggableDelegate <NSObject>
@optional
- (void)strategy:(DragStrategy*)strategy
    didStartDraggingObject:(id<Draggable>)object
        inContext:(DragContext*)context
            at:(CGPoint)point;
- (void)strategy:(DragStrategy*)strategy
    didDragObject:(id<Draggable>)object
        inContext:(DragContext*)context
            to:(CGPoint)point;
- (void)strategy:(DragStrategy*)strategy
    didStopDraggingObject:(id<Draggable>)object
        inContext:(DragContext*)context
            at:(CGPoint)point;
- (void)strategy:(DragStrategy*)strategy
    didDropObject:(id<Draggable>)object
        inContext:(DragContext*)context
            at:(CGPoint)point;
@end
```

Another example definition of Draggable is provided below:

```
@protocol Draggable <NSObject>
- (DragStrategy*)dragStrategy:(UIPanGestureRecognizer *)recognizer;
- (BOOL)canStartDraggingAt:(CGPoint)location inView:(UIView*)view;
- (UIView*)view;
- (NSMutableArray*)delegates;
@end
```

In some embodiments, tracker UI framework 214 can include an interface, "DragContext", that, when a draggable object starts dragging, establishes a context to keep track of dragging state.

An example definition of DragContext is provided below:

```
@interface DragContext : NSObject
@property (nonatomic, assign) CGPoint startLocation;
@property (nonatomic, assign) CGPoint touchLocation;
@property (nonatomic, assign) CGPoint dragLocation;
@property (nonatomic, assign) CGFloat rotationAngle;
@property (nonatomic, assign) CGFloat radialDistance;
@property (nonatomic, retain) UIView *view;
@property (nonatomic, retain) id dropArea;
@property (nonatomic, retain) UIView *draggedView;
@property (nonatomic, retain) UIView *originalView;
@property (nonatomic, assign) BOOL isCancelled;
```

```
@property (nonatomic, assign) CGFloat deviationFromStartAngle;
@property (nonatomic, assign) CGFloat deviationFromEndAngle;
@property (nonatomic, assign) CGPoint previousDragLocation;
@end
```

In some embodiments, tracker UI framework 214 can include a protocol and interface, "DragStrategy", that decouples draggable objects from the way they are dragged.

An example definition of DragStrategy (protocol) is provided below:

```
@protocol DragStrategy <NSObject>
- (void)startDraggingObject:(id<Draggable>)object
inContext:(DragContext*)context at:(CGPoint)location;
- (void)dragObject:(id<Draggable>)object
inContext:(DragContext*)context
to:(CGPoint)location;
- (void)stopDraggingObject:(id<Draggable>)object
inContext:(DragContext*)context at:(CGPoint)location;
- (void)dropObject:(id<Draggable>)object inArea:(id)dropArea
inContext:(DragContext*)context at:(CGPoint)point;
@end
```

An example definition of DragStrategy (interface) is provided below:

```
@interface DragStrategy: NSObject<DragStrategy>
@end
```

In some embodiments, tracker UI framework 214 can include an interface, "DragDropManager", that is responsible for drag and drop operations within a given tracker control. Each tracker control can have its own instance of DragDropManager. Draggable objects can be registered with DragDropManager first (e.g., using the addDraggableObject: method).

An example definition of DragDropManager is provided below:

```
@interface DragDropManager :
NSObject<UIGestureRecognizerDelegate>
@property (nonatomic, assign) BOOL enabled;
- (id)initWithView:(UIView*)view;
- (void)addDraggableObject:(id)object;
- (void)removeDraggableObject:(id)object;
+ (NSMutableArray*)globalDelegates;
@end
```

In some embodiments, tracker UI framework 214 can include an interface, "UnboundedCircularDragStrategy", that represents concrete drag and drop strategy that allows to drag event objects around trajectory of the dial circular edge. Even when a user drags outside of the dial circle, UnboundedCircularDragStrategy makes sure the dragged object sticks to the circular trajectory, allowing for very fast circular object dragging not requiring precise touch gestures.

An example of UnboundedCircularDragStrategy is provided below:

```
@interface UnboundedCircularDragStrategy : DragStrategy
/*
- (id)initWithCenter:(CGPoint)center
    radius:(CGFloat)radius;
*/
```

```
@property (nonatomic, assign) CGPoint center;
@property (nonatomic, assign) CGFloat radius;
@end
```

As disclosed, embodiments comprise a medical adherence tracker framework for tracking the adherence (or compliance) of users with workflows, such as medical adherence to medication schedules, etc. The framework can provide for serialization, persistence, synchronization, scheduling, and user interface components. The framework can provide for the integration of various third party devices that track user activity and/or measure user traits.

Several embodiments are specifically illustrated and/or described herein. However, it will be appreciated that modifications and variations of the disclosed embodiments are covered by the above teachings and within the purview of the appended claims without departing from the spirit and intended scope of the invention.

What is claimed is:

1. A non-transitory computer readable medium having instructions stored thereon that, when executed by a processor, cause the processor to implement a medical adherence tracker framework for a user provided with a workflow, the implementing comprising:

receiving, from one of a plurality of user devices over a network, a workflow definition including a plurality of nested objects that represents tasks to be completed by the user;

serializing the workflow definition, including splitting the plurality of nested objects into a plurality of separate objects, and linking the plurality of separate objects using one or more identifiers;

persisting the workflow definition, including converting the plurality of linked objects into an object graph having a plurality of nodes, each node including one of the linked objects, and assigning a unique object identifier (OI) to each node of the object graph;

synchronizing the workflow definition among the user devices, including transmitting the object graph to the user devices over the network;

receiving, from one of the user devices over the network, an updated workflow definition having an updated portion;

updating the workflow definition, including updating one of the nodes of the object graph to incorporate the updated portion of the updated workflow definition;

synchronizing the updated workflow definition among the user devices, including transmitting the updated node to the user devices over the network;

receiving, from one of the user devices over the network, user activity data generated by a tracking device connected to the user device, the tracking device having a sensor configured to capture user activity related to the tasks, the user activity data including one or more of steps taken, distance traveled, calories burned, activity intensity, sleep duration, sleep patterns, weight, body mass index (BMI), or percentage of body fat;

updating the workflow definition, including updating one of the nodes of the object graph to incorporate the user activity data to reflect progress towards completion of the tasks;

automatically synchronizing the updated workflow definition among the user devices, including transmitting the updated node to the user devices over the network;

generating a reminder to complete one or more tasks based on the updated workflow definition; and transmitting the reminder to the user devices over the network, wherein, when the updated node of the object graph is updated for a first time, a unique numeric object update identifier (OUI) is assigned to the updated node, and, when the updated node of the object graph is updated after the first time, the unique numeric OUI of the updated node is incremented.

2. The non-transitory computer readable medium of claim 1, wherein the serializing comprises serializing the workflow definition using a JavaScript Object Notation (JSON) format.

3. The non-transitory computer readable medium of claim 1, the implementing further comprising:

receiving user input and updating a portion of the workflow definition based on the user input;

persisting an updated workflow definition based on the updated portion; and synchronizing the updated workflow definition to the user devices, the synchronizing comprising transmitting, to a server, a portion of the workflow definition that has been updated.

4. The non-transitory computer readable medium of claim 1, further comprising determining whether a first object is synchronized or still needs to be synchronized based on an object synchronization state (OSS) indicator stored in a persistent storage, the OSS indicator being a numeric flag.

5. The non-transitory computer readable medium of claim 1, further comprising creating a database record for each object.

6. A system for synchronizing a workflow definition comprising one or more tasks to be completed by a user, the system comprising:

a plurality of user devices coupled to a network; and a server, coupled to the network, comprising a memory and a processor coupled to the memory, the memory having instructions stored thereon that, when executed by the processor, cause the processor to:

receive from one of the user devices over the network a workflow definition including a plurality of nested objects that represents one or more tasks to be completed by the user, serialize the workflow definition, including splitting the plurality of nested objects into a plurality of separate objects, and linking the plurality of separate objects using one or more identifiers, persist the workflow definition, including converting the plurality of linked objects into an object graph having a plurality of nodes, each node including one of the linked objects, and assigning a unique object identifier (OI) to each node of the object graph, synchronize the workflow definition among the user devices including transmitting the object graph to the user devices over the network, receive, from one of the user devices over the network, an updated workflow definition having an updated portion, update the workflow definition, including updating one of the nodes of the object graph to incorporate the updated portion of the updated workflow definition, synchronize the updated workflow definition among the user devices, including transmitting the updated node to the user devices over the network, receive, from one of the user devices over the network, user activity data generated by a tracking device connected to the user device, the tracking device having a sensor configured to capture user activity related to the tasks, the user activity data including one or more of steps taken, distance traveled, calories burned, activity intensity, sleep duration, sleep patterns, weight, body mass index (BMI), or percentage of body fat, update the workflow definition, including updating one of the nodes of the object graph to incorporate the user activity data to reflect progress towards completion of the tasks, automatically synchronize the updated workflow definition among the user devices, including transmitting the updated node to the user devices over the network, generate a reminder to complete one or more tasks based on the updated workflow definition, and transmit the reminder to the user devices over the network, wherein, when the updated node of the object graph is updated for a first time, a unique numeric object update identifier (OUI) is assigned to the updated node, and, when the updated node of the object graph is updated after the first time, the unique numeric OUI of the updated node is incremented.

7. The system of claim 6, wherein the serialize comprises serializing the workflow definition using a JavaScript Object Notation (JSON) format.

8. The system according to claim 6, further comprising an object synchronization state (OSS) indicator stored in a persistent storage, the OSS being a numeric flag that allows the system to determine if a first object is synchronized or still needs to be synchronized.

9. The system of claim 6, further comprising a separate database record for each object.

10. A computer implemented method comprising:

receiving, from one of a plurality of user devices over a network, a workflow definition including a plurality of nested objects that represents tasks to be completed by a user;

serializing the workflow definition, including splitting the plurality of nested objects into a plurality of separate objects, and linking the plurality of separate objects using one or more identifiers;

persisting the workflow definition, including converting the plurality of separate objects using one or more identifiers, and assigning a unique object identifier (OI) to each node of an object graph;

synchronizing the workflow definition among the user devices, including transmitting the object graph to the user devices over the network;

receiving, from one of the user devices over the network, an updated workflow definition having an updated portion;

updating the workflow definition, including updating one of the nodes of the object graph to incorporate the updated portion of the updated workflow definition;

synchronizing the updated workflow definition among the user devices, including transmitting the updated node to the user devices over the network;

receiving, from one of the user devices over the network, user activity data generated by a tracking device connected to the user device, the tracking device having a sensor configured to capture user activity related to the tasks, the user activity data including one or more of steps taken, distance traveled, calories burned, activity intensity, sleep duration, sleep patterns, weight, body mass index (BMI), or percentage of body fat;

updating the workflow definition, including updating one of the nodes of the object graph to incorporate user activity data to reflect progress towards completion of the tasks;

automatically synchronizing the updated workflow definition among the user devices, including transmitting the updated node to the user devices over the network;

generating a reminder to complete one or more tasks based on the updated workflow definition; and transmitting the reminder to the user devices over the network, wherein, when the updated node of the object graph is updated for a first time, a unique numeric object update identifier (OUI) is assigned to the updated node, and, when the updated node of the object graph is updated after the first time, the unique numeric OUI of the updated node is incremented.

11. The computer implemented method of claim 10, wherein the serializing comprises serializing the workflow definition using a JavaScript Object Notation (JSON) format.

12. The computer implemented method of claim 10, the method further comprising:

receiving user input and updating a portion of the workflow definition based on the user input;

persisting an updated workflow definition based on the updated portion; and synchronizing the updated workflow definition to the user devices, the synchronizing comprising transmitting, to a server, a portion of the workflow definition that has been updated.

13. The computer implemented method of claim 10, further comprising determining whether a first object is synchronized or still needs to be synchronized based on an object synchronization state (OSS) indicator stored in a persistent storage, the OSS indicator being a numeric flag.

14. The computer implemented method of claim 10, further comprising creating a database record for each object.

* * * * *

UNITED STATES PATENT AND TRADEMARK OFFICE
CERTIFICATE OF CORRECTION

PATENT NO. : 10,216,903 B2
APPLICATION NO. : 14/085987
DATED : February 26, 2019
INVENTOR(S) : Thomas et al.

It is certified that error appears in the above-identified patent and that said Letters Patent is hereby corrected as shown below:

In the Drawings

On sheet 2 of 4, in Fig. 2, under Reference Numeral 18, Line 3, delete "MEIDICAL" and insert -- MEDICAL --, therefor.

In the Specification

In Column 6, Line 38, delete "synced" and insert -- synced. --, therefor.

In Column 9, Lines 63-64, delete " $\widetilde{(\mathrm{id}}$ " and insert -- -(id --, therefor.

In Column 10, Line 24, delete "addObserver(NS" and insert -- addObserver:(NS --, therefor.

In Column 20, Line 27, delete "statefull" and insert -- stateful --, therefor.

Signed and Sealed this
Twenty-eighth Day of January, 2020

Andrei Iancu
*Director of the United States Patent and Trademark Office*